US010930386B2

(12) United States Patent
Syeda-Mahmood et al.

(10) Patent No.: US 10,930,386 B2
(45) Date of Patent: Feb. 23, 2021

(54) AUTOMATED NORMALITY SCORING OF ECHOCARDIOGRAMS

(71) Applicant: International Business Machines Corporation, Armonk, NY (US)

(72) Inventors: Tanveer F. Syeda-Mahmood, Cupertino, CA (US); Mehdi Moradi, San Jose, CA (US); Allen Lu, Bellevue, WA (US); Ehsan Dehghan Marvast, Palo Alto, CA (US)

(73) Assignee: International Business Machines Corporation, Armonk, NY (US)

( * ) Notice: Subject to any disclaimer, the term of this patent is extended or adjusted under 35 U.S.C. 154(b) by 132 days.

(21) Appl. No.: 16/215,799

(22) Filed: Dec. 11, 2018

(65) Prior Publication Data
US 2020/0185084 A1 Jun. 11, 2020

(51) Int. Cl.
| | | |
|---|---|---|
| *G16H 30/40* | (2018.01) | |
| *G16H 50/20* | (2018.01) | |
| *G06K 9/34* | (2006.01) | |
| *G06K 9/46* | (2006.01) | |
| *G06K 9/62* | (2006.01) | |
| *A61B 8/08* | (2006.01) | |

(52) U.S. Cl.
CPC ............ *G16H 30/40* (2018.01); *A61B 8/0883* (2013.01); *A61B 8/5223* (2013.01); *G06K 9/34* (2013.01); *G06K 9/4604* (2013.01); *G06K 9/6202* (2013.01); *G06K 9/6277* (2013.01); *G16H 50/20* (2018.01); *G06K 2209/05* (2013.01)

(58) Field of Classification Search
CPC ............................................. G06Q 50/22–24
See application file for complete search history.

(56) References Cited

U.S. PATENT DOCUMENTS

| | | | |
|---|---|---|---|
| 7,666,144 B2 * | 2/2010 | Cohen ............... | A61B 5/02116 600/485 |
| 7,912,528 B2 | 3/2011 | Krishnan et al. | |
| 8,577,115 B2 | 11/2013 | Gering et al. | |
| 8,698,795 B2 | 4/2014 | Grewer et al. | |

(Continued)

OTHER PUBLICATIONS

High, Rob, "The Era of Cognitive Systems: An Inside Look at IBM Watson and How it Works", IBM Corporation, Redbooks, Dec. 12, 2012, 16 pages.

(Continued)

*Primary Examiner* — Neal Sereboff
(74) *Attorney, Agent, or Firm* — Stephen J. Walder, Jr.; William J. Stock

(57) ABSTRACT

Mechanisms are provided for evaluating the normality of a medical condition of a patient based on a medical image. A medical image segmentation receives a medical image and segments the medical image to generate an extracted contour representing an anatomical feature. The medical image segmentation engine correlates the extracted contour with a template shape corresponding to the anatomical feature. A feature extraction engine extracts one or more features from a region of the medical image corresponding to the template shape. A normality classification engine performs a normality classification operation on the extracted one or more features to generate a normality score for the medical image and outputs the normality score to a computing device.

20 Claims, 4 Drawing Sheets
(1 of 4 Drawing Sheet(s) Filed in Color)

(56) References Cited

U.S. PATENT DOCUMENTS

| | | | |
|---|---|---|---|
| 8,861,891 B2 | 10/2014 | Sundar et al. | |
| 9,092,848 B2 | 7/2015 | Patwardhan et al. | |
| 9,317,927 B2 | 4/2016 | Hamarneh et al. | |
| 9,436,995 B2 | 9/2016 | Beymer et al. | |
| 9,721,338 B2 | 8/2017 | Madabhushi et al. | |
| 10,043,280 B2 | 8/2018 | Cong et al. | |
| 10,096,108 B2 | 10/2018 | Feng et al. | |
| 10,169,871 B2 | 1/2019 | Hibbard et al. | |
| 10,331,852 B2 | 6/2019 | Dormer et al. | |
| 10,460,508 B2 | 10/2019 | Zhan et al. | |
| 10,592,779 B2 | 3/2020 | Madani et al. | |
| 2003/0068074 A1 | 4/2003 | Hahn | |
| 2003/0120458 A1* | 6/2003 | Rao | G06F 19/325 702/181 |
| 2004/0022438 A1 | 2/2004 | Hibbard | |
| 2004/0208341 A1* | 10/2004 | Zhou | G06T 7/251 382/103 |
| 2005/0074154 A1* | 4/2005 | Georgescu | G06T 7/20 382/128 |
| 2005/0107704 A1* | 5/2005 | Von Behren | A61B 5/0456 600/443 |
| 2005/0147303 A1* | 7/2005 | Zhou | G06K 9/6206 382/190 |
| 2005/0209519 A1* | 9/2005 | Krishnan | G16H 50/20 600/437 |
| 2006/0008143 A1 | 1/2006 | Truyen et al. | |
| 2008/0077032 A1* | 3/2008 | Holmes | A61B 5/055 600/523 |
| 2009/0290778 A1* | 11/2009 | Sun | G06T 7/149 382/131 |
| 2010/0134517 A1 | 6/2010 | Saikaly et al. | |
| 2011/0150274 A1 | 6/2011 | Patwardhan et al. | |
| 2014/0064580 A1 | 3/2014 | Madabhushi et al. | |
| 2015/0356367 A1 | 12/2015 | Han | |
| 2018/0114313 A1 | 4/2018 | Feng et al. | |
| 2019/0059762 A1* | 2/2019 | Starr | A61B 5/0476 |
| 2019/0108635 A1 | 4/2019 | Hibbard et al. | |
| 2019/0139223 A1 | 5/2019 | Nie et al. | |
| 2019/0139227 A1 | 5/2019 | Wang et al. | |
| 2019/0139237 A1 | 5/2019 | Bresch et al. | |
| 2019/0198156 A1 | 6/2019 | Madani et al. | |
| 2019/0251693 A1 | 8/2019 | Buerger et al. | |
| 2019/0304095 A1 | 10/2019 | Veni et al. | |

OTHER PUBLICATIONS

Mahmood, Raziuddin et al., "Automatic Detection of Dilated Cardiomyopathy in Cardiac Ultrasound Videos", AMIA Symposium, Nov. 14, 2014, 7 pages.

Ronneberger, Olaf et al., "U-Net: Convolutional Networks for Biomedical Image Segmentation", International Conference on Medical Image Computing and Computer-Assisted Intervention, Springer (2015), arXiv:1505.04597v1 [cs.CV], May 18, 2015, 8 pages.

Syeda-Mahmood, Tanveer et al., "Discriminating Normal and Abnormal Left Ventricular Shapes in Four-Chamber View 2D Echocardiography", IEEE 11th International Symposium on Biomedical Imaging (ISBI 2014), Apr. 29-May 2, 2014, 4 pages.

Yuan, Michael J., "Watson and Healthcare, How natural language processing and semantic search could revolutionize clinical decision support", IBM Corporation, developerWorks, http://www.ibm.comideveloperworks/industry/library/ind-watsoni, Apr. 12, 2011, 14 pages.

* cited by examiner

AUTOMATED NORMALITY SCORING OF ECHOCARDIOGRAMS

BACKGROUND

The present application relates generally to an improved data processing apparatus and method and more specifically to mechanisms for providing automated normality scoring of echocardiograms.

An echocardiogram, also sometimes referred to as a diagnostic cardiac ultrasound, is a well-accepted medical test that uses high frequency sound waves (ultrasound) to generate an image of a patient's heart. The echocardiogram uses the sound waves to create images of the heart's chambers, valves, walls, and blood vessels (aorta, arteries, veins) attached to the heart. During an echocardiogram, a probe, referred to as a transducer, is passed over the patient's chest and is used to produce the sound waves that bounce off the structures of the heart and "echo" back to the probe. The detected "echoes" are converted into digital images that may be viewed on a computer display.

Echocardiograms are used to identify a variety of different heart conditions of patients as well as provide medical personnel information about the structure and functioning of the heart. For example, using an echocardiogram, a medical professional may be able to identify: (1) the size and shape of the heart; (2) the size, thickness, and movement of the heart's walls; (3) movement of the heart; (4) the heart's pumping strength; (5) whether or not the heart valves are working properly; (6) whether or not blood is leaking backwards through the heart valves (regurgitation); (7) whether the heart valves are too narrow (stenosis); (8) whether there is a tumor or infectious grown around the heart valves; (9) problems with the outer lining of the heart (the pericardium); (10) problems with the large blood vessels that enter and leave the heart; (11) blood clots in the chambers of the heart; and (12) abnormal holes between the chambers of the heart.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, for evaluating the normality of a medical condition of a patient based on a medical image. The method comprises receiving, by a medical image segmentation engine of the data processing system, a medical image for processing. The method further comprises performing, by the medical image segmentation engine, a segmentation operation on the medical image to generate at least one extracted contour representing an anatomical feature. In addition, the method comprises correlating, by the medical image segmentation engine, the at least one extracted contour with a template shape corresponding to the anatomical feature. Moreover, the method comprises extracting, by a feature extraction engine of the data processing system, one or more features from the medical image. The one or more features are extracted from a region of the medical image corresponding to the template shape. The method also comprises performing, by a normality classification engine of the data processing system, a normality classification operation on the extracted one or more features to generate a normality score for the medical image. Furthermore, the method comprises outputting, by the normality classification engine, the normality score to a computing device.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1A:
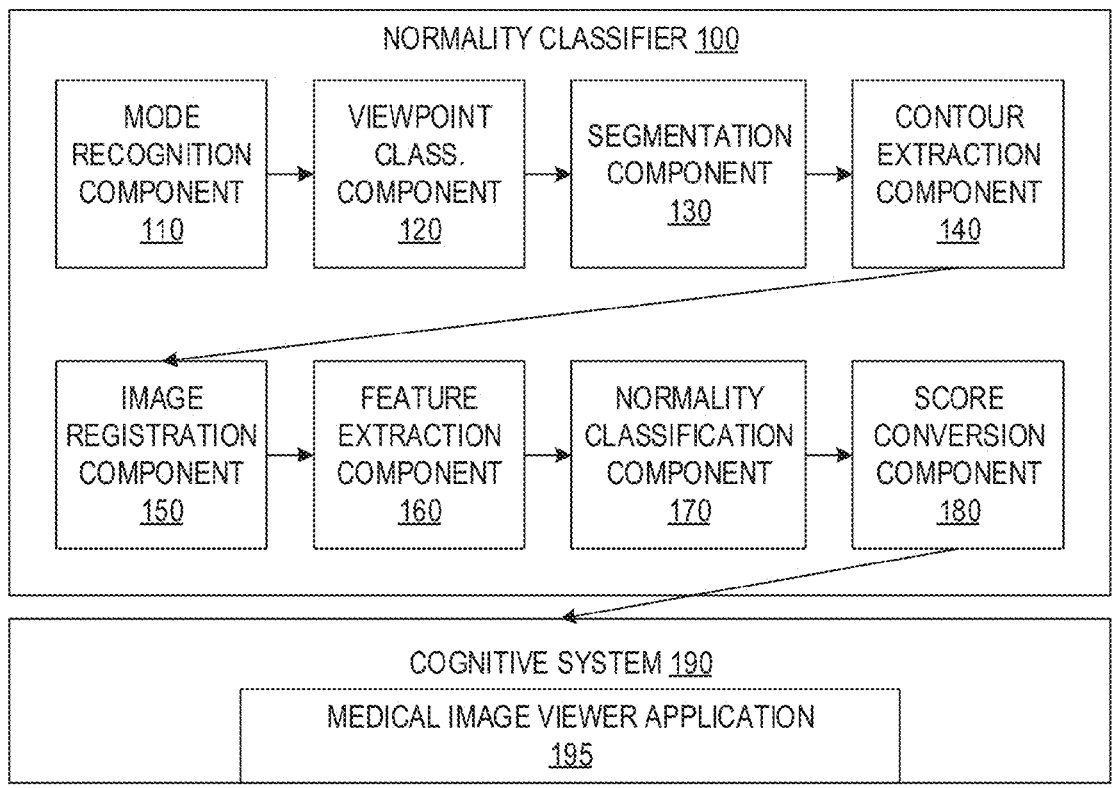
FIG. 1A is an example diagram of the primary operational components of a normality classifier in accordance with one illustrative embodiment.

As discussed above, echocardiography, i.e. the ultrasound study of the heart, is a common tool for measuring heart health with regard to a variety of factors. With echocardiography, different modes (e.g., A-mode, where a single transducer scans a line through the body with the echoes plotted as a function of depth, or B-mode which displays the acoustic impedance of a two-dimensional cross-section of tissue) and viewpoints of medical images are taken at various cardiac phases. In treating patients, it is important to be able to identify the normal appearance of echocardiograms and discriminate and score normality. Typically, normality of an echocardiogram is determined manually based on a human being who has experience in viewing such echocardiograms and has knowledge as to what elements of an echocardiogram to look for. Manual processes are time consuming, resource intensive, and subject to human error.

Thus, automated mechanisms that may themselves discriminate and score normality of an echocardiogram and/or provide decision support functionality for assisting human beings in evaluating the normality of an echocardiogram would be of great benefit. For example, automated assessment of normality from an echocardiogram is useful in referring images to the relevant cardiologists for diagnostic interpretation as well as for further follow-up operations, such as providing automated computer based cognitive treatment recommendations and performing operations for interventional planning, such as for example performing interventional planning of transcatheter aortic valve replacement (TAVR) or other procedures for addressing cardiac conditions of a patient.

It should be appreciated that, echocardiographers typically extract hundreds of measurements for assessing various diseases through echocardiography. Automated methods of normality detection may focus on key ones of these measurements, such as ejection fraction as an indicator of heart disease, or focus on a particular anatomical structure, e.g., a left ventricle only. While automating the extraction of these measurements is one research direction that may be followed, a more direct methodology is to correlate the labels of normal or abnormal with echocardiograms in designated viewpoints, and focus on deviations in image appearance as a more generally applicable approach to determining abnormality using a deep learning formulation to learn automatically the relevant features for the normal/abnormal discrimination. This more generally applicable approach or methodology employing deep learning is implemented in the mechanisms of the illustrative embodiments described herein.

The illustrative embodiments provide mechanisms for providing automated normality scoring of echocardiograms. With the mechanisms of the illustrative embodiments, a normality scoring system is provided that augments the operation of a medical image viewer and/or a cognitive healthcare system, such as a medical treatment recommendation system, interventional planning system, or the like. During training of the normality scoring system of the illustrative embodiments, a clinician performs annotation of medical images for training by selecting relevant medical images having specified modes, viewpoints, and cardiac phases, to train a deep neural network classifier, e.g., deep learning neural network model, of the normality scoring system. For example, the clinician may create atlas models for the selected modes, viewpoints, and cardiac phases for the various anatomical structures of interest, where an atlas model is a model representing an annotated medical image where the annotations may specify anatomical structure contours, abnormalities and abnormality regions or contours, measurements of anatomical structures and/or anomalies, and other information defining what is viewable in the medical image.

Deep learning tasks are then executed by the deep learning neural network model on the atlas models, where the deep learning tasks include image classification for mode, viewpoint, and cardiac phase with regional segmentation for anatomical structures, using the atlas models as a ground truth against which the operation of the deep learning neural network is measured. The training data used includes pairs of raw images and their corresponding atlases from various viewpoints and cardiac phases. Based on how well the deep learning neural network performs its segmentation and classification operations, the deep learning neural network's operational parameters, e.g., weights associated with nodes of the deep learning neural network and the like, may be adjusted so as to minimize a loss function associated with the deep learning neural network until convergence is reached, e.g., a level of improvement in the operation of the deep learning neural network between epochs is equal to or less than a threshold level of improvement.

Training image set augmentation may be performed with random rotation, scaling, and shifting, or with a generative adversarial networks (GANs) based technique for expanding a training image dataset, such as described in commonly owned and co-pending U.S. patent application Ser. Nos. 15/850,007 and 15/850,116 (P201705805US01 and P201705806US01). The images may then be normalized by subtracting mean and dividing by standard deviation. Normal/Abnormal classification of deviant shape features is thereby achieved. Classifiers such as Support Vector Machine, Random Forest, or Multi-Layer Perceptrons (MLPs) may also be used. Initial results with a 3-layer MLP on only 2 shape features showed an approximate 70% accuracy on an example sonography dataset.

At deployment, image processing and computer vision tasks are performed using the trained classifier comprising the trained deep learning neural network. In a first stage of processing of a medical image (e.g., echocardiogram) via the trained classifier comprising the trained deep learning neural network, recognition of the viewpoint, mode, and cardiac cycle phase, e.g., end-systole or end-diastole, is performed using the deep learning neural network. It should be appreciated that systole is the phase of a heartbeat when the heart muscle contracts and pumps blood from the chambers of the heart into the arteries and diastole is the phase of the heartbeat when the heart muscle relaxes and allows the chambers to fill with blood. In a second stage of processing of the medical image via the trained classifier, segmentation of major cardiac structures is performed using the trained deep learning neural network. For example, U-Net may be utilized to perform image segmentation for major cardiac structures. U-Net is described in Ronneberger et al., "U-Net: Convolutional Networks for Biomedical Image Segmentation," Computer Science Department and BIOSS Centre for Biological Signaling Studies, University of Freiburg, Germany, May 2015.

In a third stage of processing of the medical image via the trained classifier, shape deviant features are extracted and rendered as images. This includes shape registration and feature extraction with feature encoding into intensity images in one or more channels. In a fourth stage of processing of the medical image via the trained classifier, the registered shapes are classified into normal or abnormal classifications using the trained deep learning neural network of the trained classifier and corresponding normal/abnormal labels are associated with the registered shapes. In a fifth stage of processing of the medical image via the trained classifier, class likelihood probabilities are converted into a cognitive system score for assessing normality of the medical image, e.g., an echocardiogram, for the patient.

Thus, the illustrative embodiments of the present invention provide mechanisms that score medical images, e.g., echocardiograms, with regard to normality to thereby indicate whether a medical image indicates an abnormal medical condition of a patient or not. Images that have scores indicating abnormality may then be selected for presentation to a clinician for additional evaluation. Moreover, in some illustrative embodiments, the normality score may be utilized in cognitive operations performed by a cognitive system to generate treatment recommendations for providing decision support services to medical personnel. In some illustrative embodiments, the mechanisms of the illustrative embodiments may output a binary recommendation of normal or abnormal with regard to an echocardiogram, or other medical image. If the echocardiogram, for example, is classified as abnormal, it will be subsequently analyzed by the cardiologists to infer the disease. Thus, as one beneficial result of the automated operation of the illustrative embodiments, the mechanisms of the illustrative embodiments may be used by echocardiographers and cardiologists to reduce their examination workload by focusing their time and efforts on echocardiograms or medical images where abnormalities are most likely to be present. In some illustrative embodiments, the cognitive system may perform cognitive operations for performing intervention planning operations for a patient, such as scheduling of operating rooms, scheduling of personnel, scheduling medical procedures to be performed on the patient, and the like.

The automated evaluation and scoring of medical images with regard to normality/abnormality provided by the mechanisms of the illustrative embodiments may be used to assist medical personnel in quickly identifying patients for which treatment is needed, such as in a triage situation or the like. That is, the normal/abnormal probability values generated by the machine learning/deep neural network based classifier of the illustrative embodiments, and/or the cognitive system scores generated based on these probability values, may be output to a clinician or other medical person to indicate to that person how normal or abnormal a patient's condition is and provides a relative ranking of the normality/abnormality of the patient's condition relative to other patients. That is, based on the probabilities and scores generated by the mechanisms of the illustrative embodiments, the clinician or other medical personnel are automatically informed as to whether the patient's heart is normal or not based on the medical images captured of the patient's heart. Thus, based on this assessment, the medical personnel are able to focus their efforts on the more urgent cases using a relative ranking of normality.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1B:
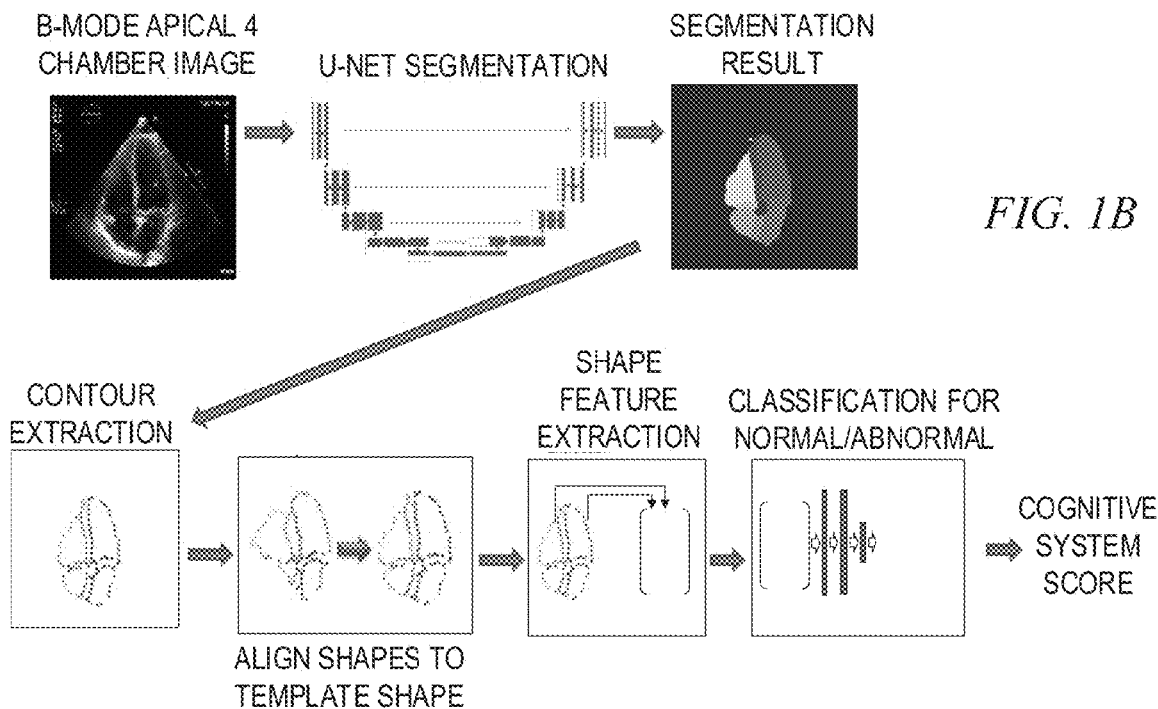
FIG. 1B is an example diagram of a workflow for classifying the normality of a medical image in accordance with one illustrative embodiment.

As noted above, the mechanisms of the illustrative embodiments classify an entire echocardiogram as representing a normal/abnormal medical condition of the patient. This capability has not been previously possible since it requires addressing many sub-problems of viewpoint detection, segmentation, and normality detection. One significant feature of the mechanisms of the illustrative embodiments, when applied to echocardiograms, is the ability to render the shape deviation of the extracted cardiovascular regions with respect to an atlas as an image so as to allow automatic feature learning through a deep learning computing system. Rather than the deep learning computing system receiving raw medical images as input, the deep learning computing system of the illustrative embodiments receive an input based on one or more error measurements between normal and abnormal shape region conglomerates. The deep learning computing system provides automatic feature learning for normal/abnormal classification and normality scoring based on such error measurements. FIGS. 1A and 1B illustrate an example diagram of the primary operational components of a normality classifier in accordance with one illustrative embodiment (FIG. 1A) and the corresponding workflow (FIG. 1B) for classifying the normality of a medical image, such as an echocardiogram, in accordance with one illustrative embodiment. The FIGS. 1A and 1B will be addressed in combination in the following description of the example operation of a normality classifier in accordance with one illustrative embodiment.

As shown in FIGS. 1A and 1B, in one illustrative embodiment, medical image classification is performed on specific viewpoints of a medical image, e.g., a B-Mode sonogram image or echocardiogram, acquired at a specific cardiac phase (e.g., end-systole or end diastole). During a first stage of operation, a mode recognition component 110, which may be implemented as a machine learning or deep learning system, such as a neural network or other machine learning/deep learning system, is utilized to identify medical images that have a specific mode and viewpoint, or otherwise classify the medical images received into various modes and viewpoints. That is, taking echocardiography as an example, such echocardiography images may be acquired with different modes (B-Mode, Doppler, M-Mode, etc.) and at different viewpoints (parasternal long axis or 2, 3, 4, 5-chamber view, etc.). Therefore, at the first stage of operation, the mode recognition component 110 analyzes the medical image to classify the medical image into different modes. The machine/deep learning system of the mode recognition component 110 may be trained using various labeled or annotated medical images that are of different modes such that the mode recognition component is able to receive a medical image, analyze characteristics of the medical image, and classify the medical image into different modes. In one illustrative embodiment, the mode recognition component 110 may be trained and may operate using Digital Imaging and Communications in Medicine (DICOM) tag analysis and image processing for the mode classification of the incoming medical images.

In one illustrative embodiment, in response to the mode recognition component 110 classifying a medical image as a mode of interest, e.g., a B-Mode image is detected with viewpoint being Apical 4 Chamber in the depicted example of FIG. 1B, a viewpoint classification component 120, which again may be implemented as a machine learning or deep learning system, may be used to classify the image into different viewpoints. The machine/deep learning viewpoint classification component 120 (or viewpoint classifier) may be trained using medical images annotated or labeled by a specialist in a training phase with the particular viewpoint information so that the trained viewpoint classification component 120 is able to classify new medical images of a particular mode of interest with regard to their viewpoint based on the similarity of the characteristics of the medical image to those upon which the training is performed.

In one illustrative embodiment, the mechanisms of the illustrative embodiments utilize cardiac atlas images formed from B-mode where chambers and valves are best visible. It should be appreciated that there are many other modes in echocardiography, such as M-mode, Doppler mode, etc. Moreover, since normal heart conditions are typically seen in 4-chamber view, this view is likely to be present in any echocardiogram and thus, the examples of the illustrative embodiments are described with reference to a 4-chamber view. It should be appreciated that the mechanisms of the illustrative embodiments are not limited to such mode or chamber view and may be applied to the other known or later developed modes or views.

Received medical images, or in some embodiments only those medical images of interest, e.g., those that match a specified mode and viewpoint as determined by the classifiers 110 and 120, are then provided to a segmentation component 130 which segments the medical images into different anatomical regions of the heart (e.g., different chambers and valves, etc.). Segmentation of a medical image is a process by which the medical image is partitioned into different meaningful segments that correspond to different tissue classes, organs, pathologies, or other biologically relevant structures. The segmentation may be performed using a machine learning or deep neural network based mechanism of the segmentation component 130, such as U-Net or the like. For purposes of illustration only, a U-Net segmentation is depicted in FIG. 1B, however the top-down atlas-based segmentation can be performed using other methods, such as deformable registration and joint label fusion.

The machine learning or deep neural network of the segmentation component 130 may be trained during a training phase based on atlases (annotated or labeled training medical images). The training data includes pairs of raw images and their created atlases from various viewpoints and cardiac phases. Training image set augmentation may be performed with random rotation, scaling, and shifting, with an automated training image generation technique, such as the GANs based technique described in commonly owned and co-pending U.S. patent application Ser. Nos. 15/850,007 and 15/850,116 (P201705805US01 and P201705806US01), or the like. The training medical images may be normalized by subtracting mean and dividing by standard deviation.

In an atlas image, the various regional contours are drawn by experts and the algorithms fill-in the regions with label color, each color representing a region label. U-net is a deep learning network that is trained to learn the mapping from raw input image data to this type of masked image depicting the various regions. Once the deep learning model of the illustrative embodiments is trained, it can be applied to any raw image to predict the location of the same masked region. Since the detections usually involve spotting the contours extracted directly from the predicted regions, and the images are noisy and not really representative of the actual contour, some smoothing is done, such as the morphological filtering that results in a better delineation of the regional contours.

Most atlases are generated for normal patients, and thus, the regional configuration they show represents normal anatomy. When a deep learning computing system is trained from such data, and is applied to an unknown patient's medical image, it will show segmentation results in that image which may not necessarily look like the ideal atlas's regional segmentation. Thus, if both medical images are registered, the deep learning computing system can assess the deviation from the expected structure to thereby identify the base representation for learning in the deep learning computing system, whether this is a normal or abnormal case. In other words, concepts being utilized in the deep learning computing system of the illustrative embodiments include the concept that abnormal cases deviate from the expected atlas and the concept of learning which types of deviation are within the normal or abnormal range, i.e. the deep learning computing system learns which features of the deviation are important for discrimination between abnormal and normal medical conditions.

After segmentation, a contour extraction component 140 identifies boundary points of the various anatomical structures identified by the segmentation. The boundary points may be identified by subtracting the segmentation mask with a morphologically eroded version of the same mask. The boundary points form a contour of the anatomical structures present in the segmentation result which may then be registered with a known template or other medical image as described hereafter.

The contours, i.e. outlines bounding shapes of anatomical structures specified by the boundary points identified by the contour extraction component 140, are rescaled via pixel spacing and rigidly registered by a medical image registration component 150, to a reference shape contour. Registration is the process by which a source medical image is aligned with a target medial image, such as a template or other known alignment of anatomical structures for the particular viewpoint, mode, etc. The source medical image is transformed, or deformed, to match the target medial image. An optimization procedure updates the transformation of the source medical image, based on a similarity value that evaluates the quality of the alignment, in an iterative manner until an optimum is found. From this alignment, anatomical features may be identified in the source medical image, based on the template annotations or labels. With the mechanisms of the illustrative embodiments, since it is not known a priori which features of the deviations are important for discrimination of normal/abnormal medical conditions, the illustrative embodiments render the deviations as an image so that the deep learning computing system can automatically select the best discriminable features and classification weights end-to-end. Thus, the feature extraction is in itself a learned model.

After registration of the contours of the medical image by the registration component 150, a feature extraction component 160 extracts anatomical shape features from the aligned boundary contours. For example, various individual or combinations of known feature extraction methodologies may be utilized by the feature extraction component 160 to perform this feature extraction. In some illustrative embodiments, shape contours may be sampled with equal arc length and concatenated to a feature matrix for classification.

In one illustrative embodiment, the mechanisms of the illustrative embodiment classify medical images by viewpoint and then select the four-chamber medical images. Thus, the illustrative embodiment employs three deep learning neural networks in a differential workflow chain, where a first deep learning neural network detects the viewpoint of the medical image, a second deep learning neural network segments the cardiac regions of interest in a 4-chamber view medical image, and a third deep learning neural network is trained and learns the deviation from normal shape features which it then applies to the segmented 4-chamber view medical image for purposes of normal/abnormal discrimination or classification of the medical image.

The shape features are fed to a normality classification component 170 (also referred to as a normality classifier), which may be implemented as a Support Vector Machine (SVM), Random Forest, Multi-Layer Perceptrons (MLP) or other machine learning or deep learning system, trained for normal/abnormal classification. The classifier outputs probabilities that, based on the features extracted by the feature extraction component 160 from the registered medical image, that the medical image represents a normal medical condition for the patient or an abnormal medical condition for the patient. For example, once the relevant features are learned by a deep learning system of the normality classification component 170, the fully connected layer of the deep learning system may be used to provide the classification of normal/abnormal, or the learned features may be separately used in a binary classifier, such as in a SVM classifier. As said previously, the key idea is this discrimination model that is made possible by obtaining a deviation image from the raw input image through the use of a segmentation model after retaining the image in an echocardiogram that depicts the relevant view.

The classification of normal/abnormal performed by the normality classification component 170 may be based on the difference between a segmented image and one or more known template images, as may be determined from the alignment of the segmented image to the known template images by the medical image registration component 150. The features extracted based on this alignment demonstrate the difference between the medical image and the template images which may then be scored, i.e. the normality classification component 170 may score the rendered feature image. In this way, the mechanisms of the illustrative embodiments may learn plural space (usually small cellular level), i.e. the space between lungs and the chest wall, pericardial space, or other small spaces in or between anatomical structures without having to train a person to annotate such spaces in medical images.

Class probabilities, e.g., normal class probability and/or abnormal class probabilities, may then be turned into a cognitive system score value by a score conversion component 180, for assessing normality of the medical image, e.g., the echocardiogram, for the patient. The cognitive system score value, or normality score, may represent a probability value using the output of a softmax layer from the deep learning computing system. The output of the softmax layer may further be enhanced by weighting the output with prevalence statistics of normal/abnormal cases using population bias.

The cognitive system score may then be output to a cognitive system 190 which may itself provide a medical image viewer application 195 and/or other cognitive operation functionality for providing decision support services or otherwise generating output that assists medical personnel in treating patients, e.g., treatment recommendation operations, performing operations for interventional planning, such as for example performing interventional planning of transcatheter aortic valve replacement (TAVR) or other procedures for addressing cardiac conditions of a patient, or the like. In some illustrative embodiments, the main utility of the normality score is a risk assessment. Once an echocardiogram is declared normal, a report may be automatically generated straight to an electronic health record system, and ultimately to a referring clinician, closing out the encounter with the patient without requiring further attention by cardiologists. However, if the classification indicates the patient's medical condition is abnormal, then the echocardiogram and report may be routed to a cardiologist so that further diagnosis and follow-up are performed. In this way, the cardiologist's workload is reduced making it both cost and time effective for the hospitals or medical practice while patients are also attended to in time and as appropriate for their needs.

In some illustrative embodiments, the cognitive system 190 may perform triage support operations by classifying medical images of patients and ranking the severity of the medical conditions of the patients at least partially based on the normality/abnormality score generated by the mechanisms of the illustrative embodiments. In this manner, the medical image viewer application of the cognitive system 190 may be automatically controlled by the cognitive system 190 to output the medical images of patients in accordance with the relative ranking of the normality of the medical images of that patient as indicated by the mechanisms of the illustrative embodiments, either alone or in addition with other cognitive evaluations of the patient's condition, e.g., evaluation of patient electronic medical record (EMR) data, other vital signs of the patient as recorded by other computing systems with which the cognitive system 190 interfaces, and the like.

Moreover, based on the identification of which medical images show abnormalities that influence the normality score generated by the mechanisms of the present invention, the corresponding most salient or relevant medical images for an individual particular patient may be output via the medical imaging viewer based on the controls of the cognitive system 190 using the information regarding normality scores of medical images for that patient as generated by the mechanisms of the illustrative embodiment. For example, there may be 20 medical images generated from the patient, each may be evaluated by the mechanisms of the illustrative embodiments to generate corresponding normality scores. The normality scores may be used relative to one another to identify which of the 20 medical images show abnormalities, e.g., normality scores showing higher probabilities of abnormal medical condition, and those medical images may be displayed to the medical professional in higher rank or order than other medical images via the medical image viewer.

In addition to normal/abnormal classification and viewing of the medical images via the medical image viewer that are more representative of abnormalities in anatomical structures, shape feature deviations (compared to shape feature of normal shapes) may be turned into intensity representations in the medical images that are rendered by the medical imaging viewer application of the cognitive system 190. That is, those portions of the medical images that have higher deviations from normal shapes as identified by the alignment and shape feature extraction and scoring of the illustrative embodiments, may be rendered in different colors, shades, with conspicuous annotations or labels, or the like, via the medical image viewer application based on the information provided by the mechanisms of the illustrative embodiments, such that the medical personnel are clearly shown the location of abnormality within the medical image. Various levels of abnormality, as determined from the normality score generated by the illustrative embodiments, may be represented in the type of accentuation of the portions of the medical image utilized to direct the medical personnel's attention to that portion of the medical image, e.g., different colors, highlighting, size of text or numerical values in annotations or labels, flashing or other visual accentuation techniques, graphical elements added to the medical image, such as symbols or pictures, or the like.

Figure 2:
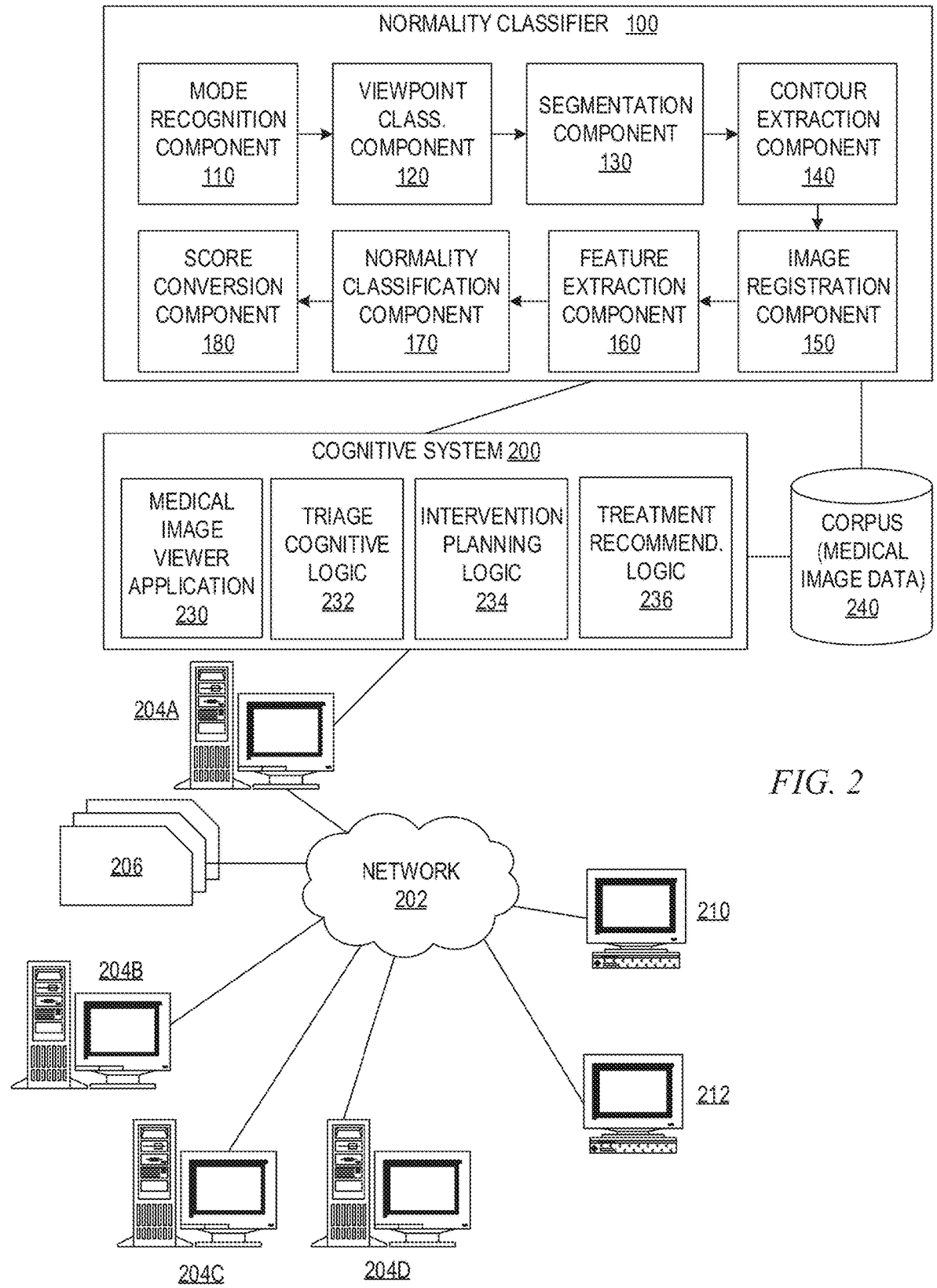
FIG. 2 depicts a schematic diagram of one illustrative embodiment of a cognitive system which operates in conjunction with a normality classifier in accordance with one illustrative embodiment.
Figure 3:
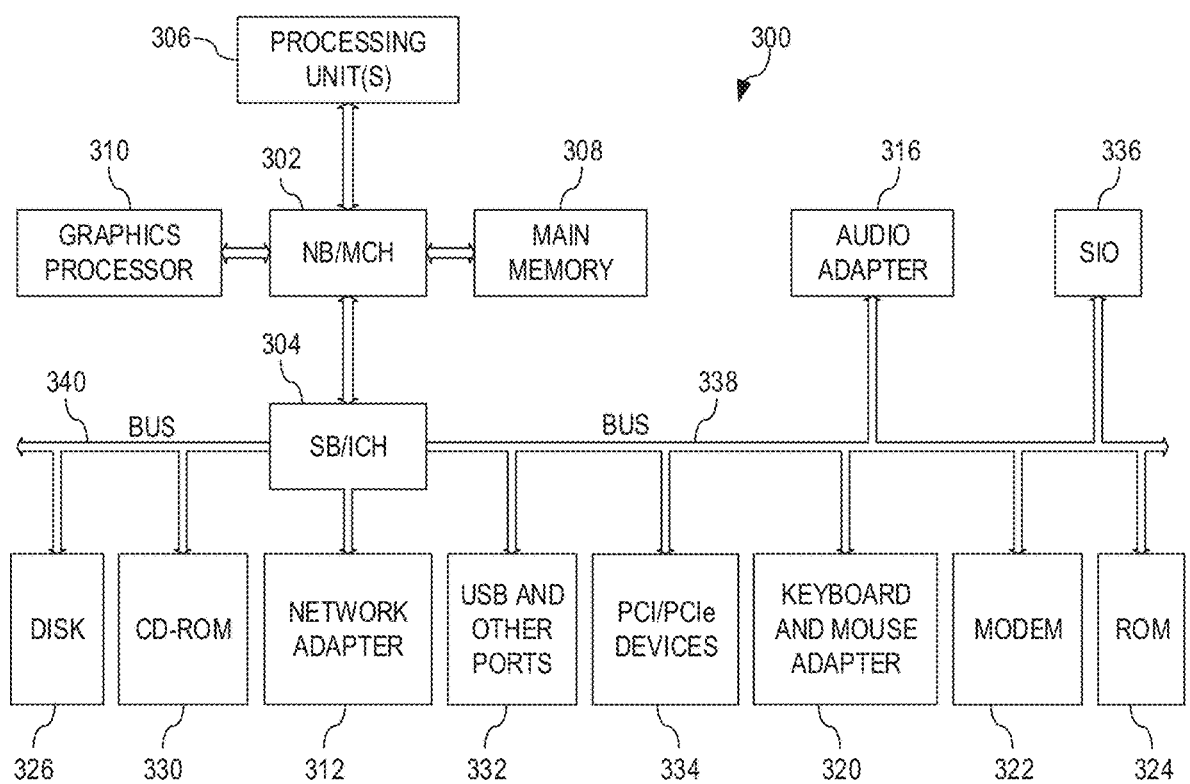
FIG. 3 is a block diagram of an example data processing system in which aspects of the illustrative embodiments are implemented.

It is clear from the above, that the illustrative embodiments may be utilized in many different types of data processing environments. In order to provide a context for the description of the specific elements and functionality of the illustrative embodiments, FIGS. 2-3 are provided hereafter as example environments in which aspects of the illustrative embodiments may be implemented. It should be appreciated that FIGS. 2-3 are only examples and are not intended to assert or imply any limitation with regard to the environments in which aspects or embodiments of the present invention may be implemented. Many modifications to the depicted environments may be made without departing from the spirit and scope of the present invention.

FIGS. 2-3 are directed to describing an example cognitive system for healthcare applications which implements a medical image viewer application 230 for viewing medical images and obtaining information about the medical images of particular patients. The cognitive system may also provide other cognitive functionality including treatment recommendations, patient electronic medical record (EMR) analysis and correlation with medical imaging data, intervention planning and scheduling operations, patient triage operations, and various other types of decision support functionality involving cognitive analysis and application of computer based artificial intelligence or cognitive logic to large volumes of data regarding patients, at least a portion of which involves the normality scoring mechanisms of the normality classifier. In some illustrative embodiments, the cognitive system may implement a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, medical image analysis logic, and the like, for example, as well as machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, medical image analysis logic, and other types of logic that emulate human thought processes using specially configured computing mechanisms. IBM Watson™ is an example of one such cognitive system with which the mechanisms of the illustrative embodiments may be utilized or in which the mechanisms of the illustrative embodiments may be implemented.

FIG. 2 depicts a schematic diagram of one illustrative embodiment of a cognitive system 200 implementing a medical image viewer application 230 in a computer network 202, and which operates in conjunction with a normality classifier, such as normality classifier 100 in FIG. 1, in accordance with one illustrative embodiment. The cognitive system 200 may further comprise various other types of cognitive operation logic for performing cognitive operations based on analysis of received medical image data and the normality scoring and classification of medical images in accordance with the operation of the normality classifier 100 as previously described above. For example, the cognitive system 200 may comprise triage cognitive logic 232, intervention planning logic 234, treatment recommendation logic 236, or other cognitive operation logic as will become apparent to those of ordinary skill in the art in view of the present description.

The cognitive system 200 is implemented on one or more computing devices 204A-D (comprising one or more processors and one or more memories, and potentially any other computing device elements generally known in the art including buses, storage devices, communication interfaces, and the like) connected to the computer network 202. For purposes of illustration only, FIG. 2 depicts the cognitive system 200 being implemented on computing device 204A only, but as noted above the cognitive system 200 may be distributed across multiple computing devices, such as a plurality of computing devices 204A-D. The network 202 includes multiple computing devices 204A-D, which may operate as server computing devices, and 210-212 which may operate as client computing devices, in communication with each other and with other devices or components via one or more wired and/or wireless data communication links, where each communication link comprises one or more of wires, routers, switches, transmitters, receivers, or the like.

In some illustrative embodiments, the cognitive system 200 and network 202 enables question processing and answer generation (QA) functionality for one or more cognitive system users via their respective computing devices 210-212. In other embodiments, the cognitive system 200 and network 202 may provide other types of cognitive operations including, but not limited to, request processing and cognitive response generation which may take many different forms depending upon the desired implementation, e.g., cognitive information retrieval, training/instruction of users, cognitive evaluation of data, such as medical imaging data, or the like. Other embodiments of the cognitive system 200 may be used with components, systems, sub-systems, and/or devices other than those that are depicted herein.

In some illustrative embodiments, the client computing devices 210 and 212 may be used as a mechanism for logging onto or otherwise accessing the cognitive system 200 for purposes of viewing medical imaging studies for patients and perform operations for classifying and/or corroborating automated classification of such medical imaging studies. For example, a radiologist or other medical imaging subject matter expert (SME) may utilize a client computing device 210 to access the services and functionality provided by the cognitive system 200 and the medical image viewer application 230 to view medical images of one or more medical imaging studies stored in the corpus 240 for one or more patients. The user of the client computing device 210 may view the medical images and perform operations for annotating the medical images, adding notes to patient electronic medical records (EMRs), corroborate automatically identified classifications of the medical images and/or override incorrect classifications, and any of a plethora of other operations that may be performed through human-computer interaction based on the human's viewing of the medical images via the cognitive system 200.

As noted above, in some illustrative embodiments, the cognitive system 200 may be configured to implement a request processing pipeline that receive inputs from various sources. The requests may be posed in the form of a natural language question, natural language request for information, natural language request for the performance of a cognitive operation, or the like. For example, the cognitive system 200 receives input from the network 202, a corpus or corpora of electronic documents 206, cognitive system users, and/or other data and other possible sources of input. In one embodiment, some or all of the inputs to the cognitive system 200 are routed through the network 202. The various computing devices 204A-D on the network 202 include access points for content creators and cognitive system users. Some of the computing devices 204A-D include devices for a database storing the corpus or corpora of data 206 (which is shown as a separate entity in FIG. 2 for illustrative purposes only). Portions of the corpus or corpora of data 206 may also be provided on one or more other network attached storage devices, in one or more databases, or other computing devices not explicitly shown in FIG. 2. The network 202 includes local network connections and remote connections in various embodiments, such that the cognitive system 200 may operate in environments of any size, including local and global, e.g., the Internet.

The request processing pipeline of the cognitive system 200 may comprises a plurality of stages for processing an input question/request based on information obtained from the corpus or corpora of data 206 and/or 240. The pipeline generates answers/responses for the input question or request based on the processing of the input question/request and the corpus or corpora of data 206, 240. In some illustrative embodiments, the cognitive system 200 may be the IBM Watson™ cognitive system available from International Business Machines Corporation of Armonk, N.Y., which is augmented with the mechanisms of the illustrative embodiments described herein. More information about the pipeline of the IBM Watson™ cognitive system may be obtained, for example, from the IBM Corporation website, IBM Redbooks, as well as in Yuan et al., "Watson and Healthcare," IBM developerWorks, 2011 and "The Era of Cognitive Systems: An Inside Look at IBM Watson and How it Works" by Rob High, IBM Redbooks, 2012.

One or more of the servers 204A-C and/or client computing devices 210-212 may be associated with medical imaging equipment (not shown), such as echocardiography equipment, sonogram equipment, magnetic resonance imaging (MRI) equipment, CT imaging equipment, and the like, which is used to capture medical image data for a patient, such as is generally known in the art. The medical images captured may be provided to a storage system such as part of a corpus or corpora of electronic data, such as corpora 206 and/or 240. The medical image data may have associated metadata generated by the equipment and/or computing systems associated with the equipment, to provide further identifiers of characteristics of the medical image, e.g., DICOM tags, metadata specifying mode, viewpoint, or the like.

As shown in FIG. 2, the cognitive system 200 may operate in conjunction with the normality classifier 100, which comprises components 110-180 which operate in the manner previously described above with regard to FIGS. 1A-1B. The various components 110-180 implementing machine learning and/or deep learning mechanisms, such as neural networks, Support Vector Machines, Random Forest systems, Multi-Layer Perceptrons (MLPs), or the like, may be trained using atlases paired with raw images in a training medical image dataset as may be provide din corpus 240, for example. These atlases may comprise labeled or annotated medical images as may have been labeled or annotated by human subject matter experts. In some embodiments, these training medical image datasets may be expanded using automated mechanisms, such as the GANs based automated mechanisms of the co-pending and commonly assigned U.S. patent applications previously referenced above.

As described previously with regard to FIGS. 1A and 1B, the normality classifier 100 may output a normality score which may indicate a probability that an input medical image represents a normal medical image or a medical image in which an abnormality is present. This normality score may be converted to a cognitive system score by the score conversion component 180 of the normality classifier 100 and provided to the cognitive system 200, or alternatively the normality score itself may be input to the cognitive system 200.

The medical image viewer application 230 and/or the other cognitive operation functionality logic 232-236 of the cognitive system 200, may utilize the normality score and/or cognitive system score for providing decision support services or otherwise generating output that assists medical personnel in treating patients. The medical image viewer application 230 and/or other cognitive operation functionality logic 232-236 may implement one or more cognitive system request processing pipelines for performing their respective operations. In some cases, each element 230-236 may be a separate request processing pipeline which operates in parallel or sequentially with the other processing pipelines to perform the respective cognitive operations.

The medical image viewer application 230 provides the logic for rendering medical images such that a user may view the medical images, manipulate the view via a graphical user interface, and the like. The medical image viewer application 230 may comprise various types of graphical user interface elements for presenting medical image information to the user, some of which may include the normality score and/or cognitive system score generated by the normality classifier 100. Based on the identification of which medical images show abnormalities that influence the normality score generated by the mechanisms of the present invention, the corresponding most salient or relevant medical images for an individual particular patient may be output via the medical imaging viewer application 230 using the information regarding normality scores of medical images for that patient as generated by the normality classifier 100, as noted above.

In some illustrative embodiments, the medical image viewer application 230 may augment the rendering of a medical image with additional emphasis and/or annotation features to identify portions of the medical image where medical personnel may wish to direct their attention, e.g., highlighting regions of abnormalities or the like. That is, in addition to normal/abnormal classification and viewing of the medical images via the medical image viewer application 230 that are more representative of abnormalities in anatomical structures, shape feature deviations (compared to shape feature of normal shapes) may be turned into intensity representations in the medical images that are rendered by the medical imaging viewer application of the cognitive system 200.

Those portions of the medical images that have higher deviations from normal shapes as identified by the alignment and shape feature extraction and scoring of the illustrative embodiments, may be rendered in different colors, shades, with conspicuous annotations or labels, or the like, via the medical image viewer application based on the information provided by the mechanisms of the illustrative embodiments, such that the medical personnel are clearly shown the location of abnormality within the medical image. Various levels of abnormality, as determined from the normality score generated by the illustrative embodiments, may be represented in the type of accentuation of the portions of the medical image utilized to direct the medical personnel's attention to that portion of the medical image, e.g., different colors, highlighting, size of text or numerical values in annotations or labels, flashing or other visual accentuation techniques, graphical elements added to the medical image, such as symbols or pictures, or the like.

In some illustrative embodiments, the cognitive system 200 may comprise triage cognitive logic 232 that performs triage support operations by classifying medical images of patients and ranking the severity of the medical conditions of the patients at least partially based on the normality/abnormality score generated by the normality classifier 100. In this manner, the medical image viewer application 230 may be automatically controlled by the triage cognitive logic 232 of the cognitive system 200 to output the medical images of patients in accordance with the relative ranking of the normality of the medical images of that patient as indicated by the mechanisms of the illustrative embodiments, either alone or in addition with other cognitive evaluations of the patient's condition, e.g., evaluation of patient electronic medical record (EMR) data, other vital signs of the patient as recorded by other computing systems 204A-C or client devices 210-212, with which the cognitive system 200 interfaces, and the like.

In some illustrative embodiments, treatment recommendation logic 236 may be implemented by the cognitive system 200 which may utilize the normality score or cognitive system score generated by the normality classifier 100, along with other cognitive processing of patient information, such as may be provided in one or more patient electronic medical records (EMRs) as may be provided by corpus/corpora 206 and/or 240, to determine a treatment to be recommended to medical personnel for treating the patient. The treatment recommendation logic 236 may apply medical knowledge encoded in various sources of medical information in electronic form in the corpus or corpora 206 and/or 240 to the patient information and/or normality score generated by the normality classifier 100 to determine the applicability of various candidate treatments. The candidate treatments may be evaluated based on evidential data to generate confidence scores for the various candidate treatments, and a final recommended treatment may be generated based on a ranking of the candidate treatments based on the confidence scores. In some embodiments, the normality score and/or cognitive system score generated by the normality classifier 100 may be used as part of the calculation of confidence scores for the various candidate treatments, e.g., as an additional scoring variable, as a weighting factor, or the like.

In some illustrative embodiments, the normality scoring and ranking of patient medical conditions based on the evaluation of normality performed by the normality classifier 100 may be used by intervention planning logic 234 of the cognitive system 200 to perform intervention planning operations for planning procedures and services to treat patients based on a relative ranking of severity of patient medical conditions. For example, the normality score generated by the normality classifier 100 may be used by the cognitive system 200 to relatively rank patients, such as discussed above with the triage cognitive logic 232. The intervention planning logic 234 may identify relative severity of patient medical conditions and perform operations interactive with other facility systems, such as scheduling systems for scheduling medical personnel to treat the patient, scheduling access to facilities for performing needed procedures, scheduling medical personnel for performing medical procedures, schedule medical equipment that is to be used to perform such medical procedures, and the like. This may be done automatically and/or semi-automatically with the assistance of other human users that are involved in scheduling or otherwise performing intervention planning operations. For example, the intervention planning logic 234, potentially interacting with triage cognitive logic 232 and treatment recommendation logic 236, may send requests to personnel for specific medical procedures to be scheduled, or may go further and determine what facilities, equipment, and personnel are needed to perform a medical procedure and send specific requests for these particular facilities, equipment, and personnel, with the subsequent scheduling being done manually by the human personnel.

It should be appreciated that these are only examples of cognitive operations that may be performed based on a determination of normality by the normality classifier 100 and the corresponding normality score and/or cognitive system score generated by the normality classifier 100. Other types of cognitive operations that may be performed in addition to, or in replacement of, those shown in FIG. 2 may be used without departing from the spirit and scope of the present invention.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 8 is provided as an example of one type of data processing system in which aspects of the present invention may be implemented. Many other types of data processing systems may be likewise configured to specifically implement the mechanisms of the illustrative embodiments.

FIG. 3 is a block diagram of an example data processing system in which aspects of the illustrative embodiments are implemented. Data processing system 800 is an example of a computer, such as a server 204A-D or client 210-212 in FIG. 2, in which computer usable code or instructions implementing the processes for illustrative embodiments of the present invention are located. In one illustrative embodiment, FIG. 3 represents a server computing device, such as a server 204A, which, which implements a cognitive system 200 and medical image viewer application 230, where the server 204A further is specifically configured and executes hardware and/or software logic to implement the normality classifier 100 of FIGS. 1A and 2.

In the depicted example, data processing system 300 employs a hub architecture including North Bridge and Memory Controller Hub (NB/MCH) 302 and South Bridge and Input/Output (I/O) Controller Hub (SB/ICH) 304. Processing unit 306, main memory 308, and graphics processor 310 are connected to NB/MCH 302. Graphics processor 310 is connected to NB/MCH 302 through an accelerated graphics port (AGP).

In the depicted example, local area network (LAN) adapter 312 connects to SB/ICH 304. Audio adapter 316, keyboard and mouse adapter 320, modem 322, read only memory (ROM) 324, hard disk drive (HDD) 326, CD-ROM drive 330, universal serial bus (USB) ports and other communication ports 332, and PCI/PCIe devices 334 connect to SB/ICH 304 through bus 338 and bus 340. PCI/PCIe devices may include, for example, Ethernet adapters, add-in cards, and PC cards for notebook computers. PCI uses a card bus controller, while PCIe does not. ROM 324 may be, for example, a flash basic input/output system (BIOS).

HDD 326 and CD-ROM drive 330 connect to SB/ICH 304 through bus 340. HDD 326 and CD-ROM drive 330 may use, for example, an integrated drive electronics (IDE) or serial advanced technology attachment (SATA) interface. Super I/O (SIO) device 336 is connected to SB/ICH 304.

An operating system runs on processing unit 306. The operating system coordinates and provides control of various components within the data processing system 300 in FIG. 3. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 300.

As a server, data processing system 300 may be, for example, an IBM® eServer™ System p® computer system, running the Advanced Interactive Executive) (AIX®) operating system or the LINUX® operating system. Data processing system 300 may be a symmetric multiprocessor (SMP) system including a plurality of processors in processing unit 306. Alternatively, a single processor system may be employed.

Instructions for the operating system, the object-oriented programming system, and applications or programs are located on storage devices, such as HDD 326, and are loaded into main memory 308 for execution by processing unit 306. The processes for illustrative embodiments of the present invention are performed by processing unit 306 using computer usable program code, which is located in a memory such as, for example, main memory 308, ROM 324, or in one or more peripheral devices 326 and 330, for example.

A bus system, such as bus 338 or bus 340 as shown in FIG. 3, is comprised of one or more buses. Of course, the bus system may be implemented using any type of communication fabric or architecture that provides for a transfer of data between different components or devices attached to the fabric or architecture. A communication unit, such as modem 322 or network adapter 312 of FIG. 3, includes one or more devices used to transmit and receive data. A memory may be, for example, main memory 308, ROM 324, or a cache such as found in NB/MCH 302 in FIG. 3.

Those of ordinary skill in the art will appreciate that the hardware depicted in FIGS. 2 and 3 may vary depending on the implementation. Other internal hardware or peripheral devices, such as flash memory, equivalent non-volatile memory, or optical disk drives and the like, may be used in addition to or in place of the hardware depicted in FIGS. 2 and 3. Also, the processes of the illustrative embodiments may be applied to a multiprocessor data processing system, other than the SMP system mentioned previously, without departing from the spirit and scope of the present invention.

Moreover, the data processing system 300 may take the form of any of a number of different data processing systems including client computing devices, server computing devices, a tablet computer, laptop computer, telephone or other communication device, a personal digital assistant (PDA), or the like. In some illustrative examples, data processing system 300 may be a portable computing device that is configured with flash memory to provide non-volatile memory for storing operating system files and/or user-generated data, for example. Essentially, data processing system 300 may be any known or later developed data processing system without architectural limitation.

Figure 4:
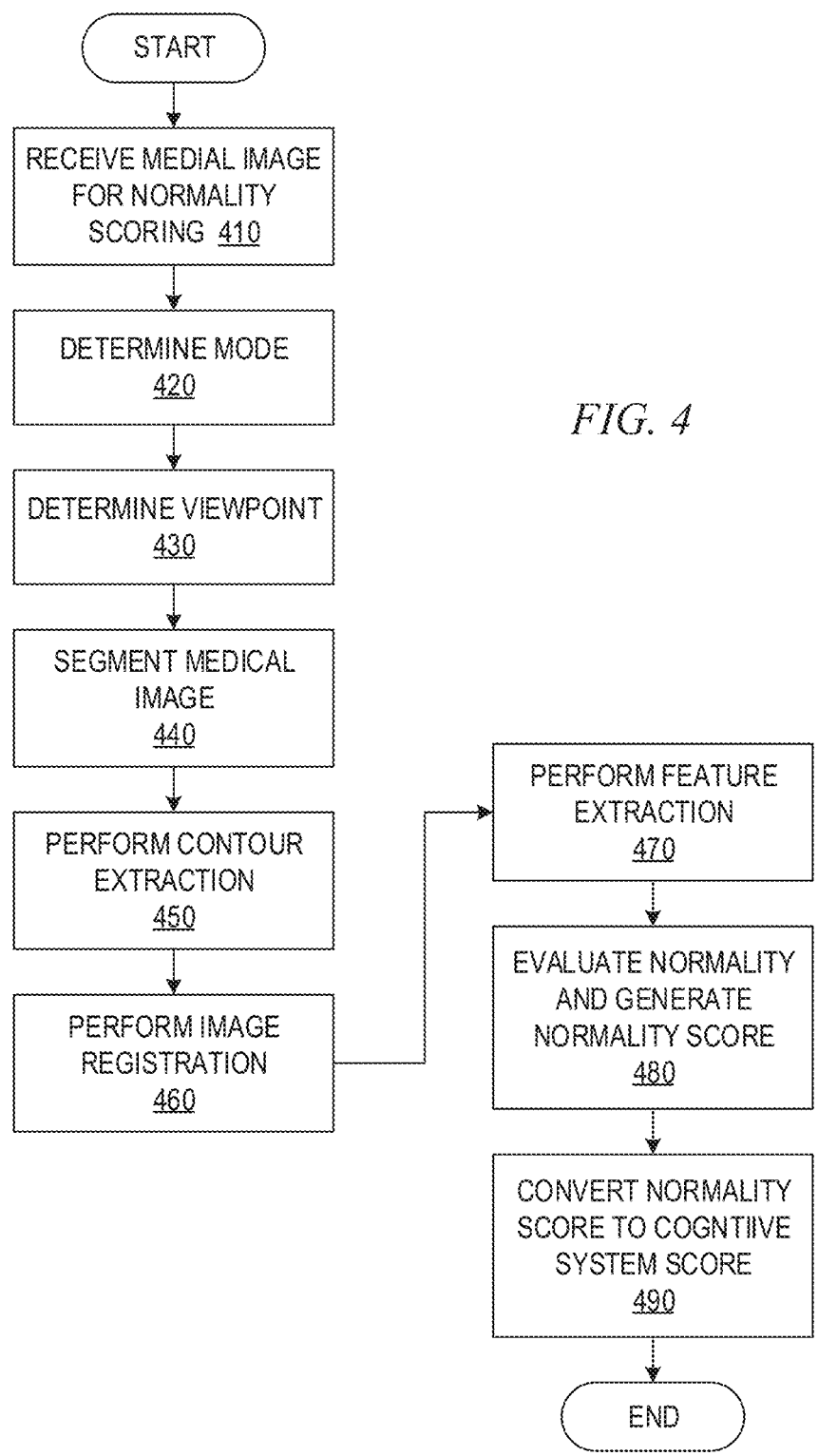
FIG. 4 is a flowchart outlining an example operation for performing normality classification of medical images in accordance with one illustrative embodiment.

FIG. 4 is a flowchart outlining an example operation for performing normality classification of medical images in accordance with one illustrative embodiment. The operation outlined in FIG. 4 may be implemented by a normality classification system, such as normality classifier 100 described above with regard to FIGS. 1A and 2. The operation outlined in FIG. 4 is for purposes of generating the normality score and corresponding cognitive system score based on an evaluation of the normality or abnormality of the anatomical structures found in an input medical image. The operation assumes that the various machine learning and/or deep learning mechanisms have already been trained in the manner previously described above. Moreover, while not shown in FIG. 4, the normality score and/or cognitive system score may be used as a basis for performing medical image rendering by a medical image viewer application and/or may be used as a basis for performing various cognitive operations.

As shown in FIG. 4, the operation starts by receiving a medical image for normality scoring (step 410). The mode of the received medical image is determined (step 420) and the viewpoint of the medical image is classified (step 430). The mode and viewpoint may be used as a basis for determining whether additional normality scoring operations are to be performed, i.e. whether or not the medical image received is a type of medical image of interest, e.g., B-Mode. Moreover, the determination of mode and viewpoint may be used as a basis for retrieving appropriate templates and the like for performing additional operations for segmentation, contour extraction, registration and feature extraction, for example. It is assumed for purposes of this description that the medical image received is of the type that further normality scoring is to be performed or that all received medical images are always scored for normality.

The medical image is segmented into anatomical structure regions (step 440) and contours of the anatomical structures are extracted based on the segmentation (step 450). The image is then registered using a corresponding medical image template (step 460) and corresponding features are extracted from the registered image (step 470). Based on the extracted features, normality of the medical image is evaluated to generate a normality score (step 480). The normality score is then converted to a cognitive system score which is output to the cognitive system for use in presenting medical images via a medical image viewer and/or to perform other cognitive operations (step 490). The operation then terminates.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, for evaluating the normality of a medical condition of a patient based on a medical image, the method comprising:

receiving, by a medical image segmentation engine of the data processing system, a medical image for processing;

performing, by the medical image segmentation engine, a segmentation operation on the medical image to generate at least one extracted contour representing an anatomical feature;

performing image registration, by the medical image segmentation engine, of the at least one extracted contour with a template shape corresponding to the anatomical feature at least by deforming the at least one extracted contour to match the template shape and thereby identify a region of the medical image that corresponds to a shape of the template shape;

extracting, by a feature extraction engine of the data processing system, one or more features from the medical image, wherein the one or more features are extracted from the region of the medical image corresponding to the template shape identified by the image registration and represent deviation features, indicating a deviation of the at least one extracted contour from the template shape;

performing, by a normality classification engine of the data processing system, a normality classification operation on the extracted one or more features to generate a normality score for the medical image, wherein the normality classification engine comprises a deep learning neural network trained to classify deviations of the at least one extracted contour from the template shape with regard to normality of the deviations, and wherein the normality score indicates a probability of the medical condition of the patient, as represented in the medical image, being normal or abnormal based on the deviations; and outputting, by the normality classification engine, the normality score to a computing device.

2. The method of claim 1, wherein performing image registration comprises detecting deviations of the at least one extracted contour from the template shape corresponding to the anatomical feature, and wherein the one or more features extracted are features associated with the detected deviations.

3. The method of claim 1, wherein performing the normality classification operation on the extracted one or more features to generate a normality score for the medical image comprises processing, by the trained deep learning neural network, the one or more extracted features to generate one or more probability values indicating a probability that the one or more extracted features are associated with a normal or abnormal medical condition.

4. The method of claim 1, further comprising:
determining, by the normality classification engine, whether or not the medical image is abnormal or not based on the normality score; and
in response to determining that the medical image is abnormal, presenting the medical image via a medical image viewer application of the computing device for manual review by a clinician.

5. The method of claim 4, wherein the medical image is one of a plurality of medical images, and wherein only medical images, in the plurality of medical images, determined to be abnormal by the normality classification engine, are presented via the medical image viewer application of the computing device.

6. The method of claim 1, wherein extracting one or more features from the medical image comprises encoding the one or more extracted features into one or more intensity images in one or more channels.

7. The method of claim 1, wherein performing the normality classification operation on the extracted one or more features comprises:
processing the medical image via the trained deep learning neural network to classify the at least one extracted contour into a normal classification or abnormal classification; and
applying to the at least one extracted contour, a corresponding metadata label indicating whether or not the at least one extracted contour is classified as a normal classification or abnormal classification.

8. The method of claim 7, wherein performing the normality classification operation further comprises converting probability values generated by the trained deep learning neural network in association with the normal classification and abnormal classification, for the at least one extracted contour, into the normality score for the medical image.

9. The method of claim 1, wherein the medical image is an echocardiogram received from an echocardiograph imaging system.

10. The method of claim 1, wherein outputting, by the normality classification engine, the normality score to a computing device comprises:
outputting, via a medical imaging viewer application executing on the computing device, a graphical representation of the medical image with an intensity representation in the medical image showing portions of the medical image that have relatively higher deviations from the template shape, as determined by the normality classification operation, with different colors, shades, annotations, or labels different from other portions of the medical image with relatively lower deviations from the template shape, as determined by the normality classification operation.

11. A computer program product comprising a computer readable storage medium having a computer readable program stored therein, wherein the computer readable program, when executed on a data processing system, causes the data processing system to:
receive, by a medical image segmentation engine of the data processing system, a medical image for processing;
perform, by the medical image segmentation engine, a segmentation operation on the medical image to generate at least one extracted contour representing an anatomical feature;
perform image registration, by the medical image segmentation engine, of the at least one extracted contour with a template shape corresponding to the anatomical feature at least by deforming the at least one extracted contour to match the template shape and thereby identify a region of the medical image that corresponds to a shape of the template shape;
extract, by a feature extraction engine of the data processing system, one or more features from the medical image, wherein the one or more features are extracted from the region of the medical image corresponding to the template shape identified by the image registration and represent deviation features, indicating a deviation of the at least one extracted contour from the template shape;
perform, by a normality classification engine of the data processing system, a normality classification operation on the extracted one or more features to generate a normality score for the medical image, wherein the normality classification engine comprises a deep learning neural network trained to classify deviations of the at least one extracted contour from the template shape with regard to normality of the deviations, and wherein the normality score indicates a probability of the medical condition of the patient, as represented in the medical image, being normal or abnormal based on the deviations; and
output, by the normality classification engine, the normality score to a computing device.

12. The computer program product of claim 11, wherein the computer readable program further causes the data processing system to perform image registration at least by detecting deviations of the at least one extracted contour from the template shape corresponding to the anatomical feature, and wherein the one or more features extracted are features associated with the detected deviations.

13. The computer program product of claim 11, wherein the computer readable program further causes the data processing system to perform the normality classification operation on the extracted one or more features to generate a normality score for the medical image at least by processing, by the trained deep learning neural network, the one or more extracted features to generate one or more probability values indicating a probability that the one or more extracted features are associated with a normal or abnormal medical condition.

14. The computer program product of claim 11, wherein the computer readable program further causes the data processing system to:
determine, by the normality classification engine, whether or not the medical image is abnormal or not based on the normality score; and in response to determining that the medical image is abnormal, present the medical image via a medical image viewer application of the computing device for manual review by a clinician.

15. The computer program product of claim 14, wherein the medical image is one of a plurality of medical images, and wherein only medical images, in the plurality of medical images, determined to be abnormal by the normality classification engine, are presented via the medical image viewer application of the computing device.

16. The computer program product of claim 11, wherein the computer readable program further causes the data processing system to extract one or more features from the medical image at least by encoding the one or more extracted features into one or more intensity images in one or more channels.

17. The computer program product of claim 11, wherein the computer readable program further causes the data processing system to perform the normality classification operation on the extracted one or more features at least by:
processing the medical image via the trained deep learning neural network model to classify the at least one extracted contour into a normal classification or abnormal classification; and
applying to the at least one extracted contour, a corresponding metadata label indicating whether or not the at least one extracted contour is classified as a normal classification or abnormal classification.

18. The computer program product of claim 17, wherein the computer readable program further causes the data processing system to perform the normality classification operation further at least by converting probability values generated by the trained deep learning neural network in association with the normal classification and abnormal classification, for the at least one extracted contour, into the normality score for the medical image.

19. The computer program product of claim 11, wherein the medical image is an echocardiogram received from an echocardiograph imaging system.

20. An apparatus comprising:
at least one processor; and
at least one memory coupled to the at least one processor, wherein the at least one memory comprises instructions which, when executed by the at least one processor, cause the at least one processor to:
receive, by a medical image segmentation engine executing on the at least one processor, a medical image for processing;
perform, by the medical image segmentation engine, a segmentation operation on the medical image to generate at least one extracted contour representing an anatomical feature;
perform image registration, by the medical image segmentation engine, of the at least one extracted contour with a template shape corresponding to the anatomical feature at least by deforming the at least one extracted contour to match the template shape and thereby identify a region of the medical image that corresponds to a shape of the template shape;
extract, by a feature extraction engine executing on the at least one processor, one or more features from the medical image, wherein the one or more features are extracted from the region of the medical image corresponding to the template shape identified by the image registration and represent deviation features, indicating a deviation of the at least one extracted contour from the template shape;
perform, by a normality classification engine executing on the at least one processor, a normality classification operation on the extracted one or more features to generate a normality score for the medical image, wherein the normality classification engine comprises a deep learning neural network trained to classify deviations of the at least one extracted contour from the template shape with regard to normality of the deviations, and wherein the normality score indicates a probability of the medical condition of the patient, as represented in the medical image, being normal or abnormal based on the deviations; and
output, by the normality classification engine, the normality score to a computing device.

\* \* \* \* \*